(12) United States Patent
Zhu et al.

(10) Patent No.: US 12,226,784 B2
(45) Date of Patent: Feb. 18, 2025

(54) MAGNETIC BEAD PURIFICATION SYSTEM

(71) Applicant: Nanjing GenScript Biotech Co., Ltd., Jiangsu (CN)

(72) Inventors: Jinxin Zhu, Jiangsu (CN); Ruina He, Jiangsu (CN); Hong Qian, Jiangsu (CN); Tao Bai, Jiangsu (CN); Deming Li, Jiangsu (CN); Cheng Zheng, Jiangsu (CN); Guodong Chen, Jiangsu (CN)

(73) Assignee: Nanjing GenScript Biotech Co., Ltd., Jiangsu (CN)

( * ) Notice: Subject to any disclaimer, the term of this patent is extended or adjusted under 35 U.S.C. 154(b) by 459 days.

(21) Appl. No.: 17/051,119

(22) PCT Filed: Apr. 26, 2019

(86) PCT No.: PCT/CN2019/084590
§ 371 (c)(1),
(2) Date: Oct. 27, 2020

(87) PCT Pub. No.: WO2019/206284
PCT Pub. Date: Oct. 31, 2019

(65) Prior Publication Data
US 2021/0299677 A1    Sep. 30, 2021

(30) Foreign Application Priority Data

Apr. 28, 2018  (CN) .......................... 201810403510.1

(51) Int. Cl.
*B03C 1/28*     (2006.01)
*C07K 1/14*     (2006.01)
(Continued)

(52) U.S. Cl.
CPC ............... *B03C 1/288* (2013.01); *C07K 1/14* (2013.01); *C12M 1/42* (2013.01); *C12M 33/06* (2013.01);
(Continued)

(58) Field of Classification Search
CPC ............................ C07K 1/14; B03C 2201/18
See application file for complete search history.

(56) References Cited

U.S. PATENT DOCUMENTS

2016/0039615 A1\* 2/2016 Otts ....................... G01N 35/04
                                                                  198/368
2016/0245834 A1\* 8/2016 Liu ......................... C12M 33/06
(Continued)

FOREIGN PATENT DOCUMENTS

CN          104450498 A        3/2015
CN          105821482 A        8/2016
(Continued)

OTHER PUBLICATIONS

Huang et al., CN104450498A Nucleic acid extractor translated Description, 2015, EPO (Year: 2015).*
(Continued)

*Primary Examiner* — Maris R Kessel
*Assistant Examiner* — Mickey Huang
(74) *Attorney, Agent, or Firm* — Klarquist Sparkman, LLP

(57) ABSTRACT

The present invention provides a magnetic bead purification system, including: a housing; a liquid path treatment system provided inside the housing, the liquid path treatment system being connectable to a reagent barrel and a waste liquid barrel; a sample addition needle group connected to the liquid path treatment system, the sample addition needle group being movable within the housing and connected to the liquid path treatment system, so as to receive a reagent (Continued)

from the liquid path treatment system or to discharge a waste liquid to the liquid path treatment system; a purification magnetic separation system, including a magnetic element, the purification magnetic separation system being controllable to apply a lateral magnetic force to a purification treatment position inside the housing or stop the application of the magnetic force by the magnetic element; and a purification station system movable between a purification treatment position inside the housing and a loading position outside the housing, the purification station system being adapted to load a container. The magnetic bead purification system of the present invention can easily achieve large capacity sample treatment.

14 Claims, 9 Drawing Sheets

(51) Int. Cl.
  *C12M 1/00* (2006.01)
  *C12M 1/32* (2006.01)
  *C12M 1/42* (2006.01)
  *C12N 15/10* (2006.01)
(52) U.S. Cl.
  CPC ............ *C12M 47/04* (2013.01); *C12M 47/12* (2013.01); *C12N 15/1013* (2013.01); *B03C 2201/18* (2013.01)

(56) References Cited

U.S. PATENT DOCUMENTS

2017/0059599 A1* 3/2017 Riether .................. G01N 35/04
2019/0145968 A1* 5/2019 Wang ...................... B01L 9/523
                                                                        506/3

FOREIGN PATENT DOCUMENTS

| CN | 208586235 U | 3/2019 | |
| JP | 58-162287 A | 9/1983 | |
| JP | 7-110333 A | 4/1995 | |
| WO | WO-2018002429 A1 * | 1/2018 | ................ B01L 9/06 |

OTHER PUBLICATIONS

Li Xingjun, CN 105821482 A Biochemical micro-reaction system, high-throughput sequencing database builder and application translated Description and claims, 2016, EPO (Year: 2016).*

International Search Report for PCT/CN2019/084590, English Translation submitted herewith.

International Search Report and Written Opinion for International Application No. PCT/CN2019/084590, mailed on Jul. 25, 2019 (8 pages).

English translation of International Search Report for International Application No. PCT/CN2019/084590, mailed on Jul. 25, 2019 (2 pages).

* cited by examiner

MAGNETIC BEAD PURIFICATION SYSTEM

CROSS REFERENCE TO RELATED APPLICATIONS

This is the U.S. National Stage of International Application No. PCT/CN2019/084590, filed Apr. 26, 2019, which was published in Chinese under PCT Article 21(2), which in turn claims the benefit of China Application No. 201810403510.1, filed Apr. 28, 2018.

BACKGROUND

Technical Field

The present invention relates to a magnetic bead purification system for purifying substances such as proteins and nucleic acids.

Related Art

Usually, a magnetic bead purification method uses a purification system to separate magnetic beads through a magnetic field to achieve the objective of separating and purifying substances such as cells, proteins, or nucleic acids. Compared with commonly used precipitation method, centrifugation method and column membrane method, the magnetic bead purification method has the characteristics of high extraction efficiency, high separation rate, low equipment requirements, and the like.

Compared with resin purification, a magnetic bead purification method based on magnetic attraction relies on the combination of the principle of magnetic forces and incubation to quickly and effectively enrich target proteins in samples, thereby effectively avoiding the disadvantages such as limitations of resin on sample pretreatment s and sample loading methods, and overcoming limitations on column packing and flow rate. A purification method using magnetic separation achieves automation more easily, and can meet a high-throughput purification requirement for rapid, automatic, and multi-channel simultaneous treatment.

At the present, the only magnetic bead purification equipment available on the market is the Kingfisher automatic magnetic bead protein purification instrument launched by Thermo Scientific, which uses the magnetic bead method that a magnetic rod is inserted into a container to purify proteins. However, it can purify a maximum sample volume of at most 5 ml, requires manual participation during liquid transferring treatment, and adopts open type work stations which are not conducive for contamination control, and therefore cannot meet the needs of customers for automatic treatment of tens of milliliters and one or two hundred milliliters of samples.

Therefore, there is a need to improve a magnetic bead purification system.

SUMMARY OF THE INVENTION

A magnetic bead purification system according to the present invention can easily achieve large capacity sample treatment.

The present invention discloses a magnetic bead purification system, including: a housing; a liquid path treatment system provided inside the housing, the liquid path treatment system being connectable to a reagent barrel and a waste liquid barrel; a sample addition needle group connected to the liquid path treatment system, the sample addition needle group being movable within the housing and connected to the liquid path treatment system, so as to receive a reagent from the liquid path treatment system or to discharge a waste liquid to the liquid path treatment system; a purification magnetic separation system, including a magnetic element, the purification magnetic separation system being controllable to apply a lateral magnetic force to a purification treatment position inside the housing or stop the application of the magnetic force by the magnetic element; and a purification station system movable between a purification treatment position inside the housing and a loading position outside the housing, the purification station system being adapted to load a container.

Preferably, the magnetic element is a permanent magnet; the purification magnetic separation system is controlled to apply the magnetic force or to stop the application of the magnetic force by moving the magnetic element towards and away from the purification treatment position.

Preferably, the purification magnetic separation system includes a driving system, a sliding system and a transmission system, so as to move the magnetic element towards and away from the purification treatment position.

Preferably, the magnetic element is an electromagnet; the purification magnetic separation system is controlled to apply the magnetic force or to stop the application of the magnetic force by controlling on and off of the electromagnet.

Preferably, the purification station system includes a sliding system, and is driven by a driving device to move from the purification treatment position to the loading position.

Preferably, the purification station system includes a magnetic absorption block, so as to move from the loading position to the purification treatment position by the magnetic force of the magnetic element.

Preferably, when a container filled with a mixed liquid of incubated crude proteins and magnetic beads is mounted on the purification station system, and the purification station system moves into the purification treatment position, the purification magnetic separation system applies the lateral magnetic force to attract the magnetic beads onto a container wall of the container.

Preferably, the purification station system includes two purification station brackets, and each purification station bracket includes at least one adaptation hole for a purification container.

Preferably, the sample addition needle group is a variable-spacing sample addition needle group.

Preferably, the variable-spacing sample addition needle group includes a fixed type sample addition needle fixing block and a movable type sample addition needle fixing block which are configured to mount sample addition needles, and the movable type sample addition needle fixing block is movable to adjust a spacing between the sample addition needles in the sample addition needle group.

Preferably, the variable-spacing sample addition needle group includes more than one movable type sample addition needle fixing block.

Preferably, the sample addition needle group includes an elastic mechanism for up-and-down trace movement of the sample addition needles.

Preferably, the sample addition needles of the sample addition needle group include waste discharging needle holes configured to discharge waste liquid and sample addition needle holes configured to add reagents.

Preferably, the sample addition needle holes are also configured for spray rinsing of the container wall and bubble blowing.

Preferably, the magnetic bead purification system further includes a mechanical arm provided inside the housing, and the sample addition needle group is mounted on the mechanical arm to realize movement.

Preferably, the magnetic bead purification system includes a cleaning module for cleaning the sample addition needles.

Preferably, the cleaning module includes cleaning liquid addition holes paired with the sample addition needles, a liquid discharging hole, a cleaning slot and a cleaning liquid discharging slot.

Preferably, the magnetic bead purification system further includes a control system; and the control system automatically controls operation of each component of the magnetic bead purification system according to settings.

Preferably, the magnetic bead purification system further includes a contamination control system, and the contamination control system includes a wind path filtering system and an ultraviolet sterilization system.

Preferably, the purification station system includes a fixing device to load a six-hole container.

BRIEF DESCRIPTION OF THE DRAWINGS

The accompanying drawings illustrate a magnetic bead purification system and components of preferable embodiments according to the present invention.

The drawings are illustrative descriptions only, and not necessarily drawn to scale.

DETAILED DESCRIPTION OF THE INVENTION

To describe the technical solutions in the embodiments of the present invention more clearly, the following introduces the accompanying drawings for describing the specific implements of the present invention. Apparently, the accompanying drawings in the following descriptions show merely some exemplary embodiments of the present invention.

The present invention discloses a semi-automatic magnetic bead purification system. The semi-automatic magnetic bead purification system according to the present invention uses a magnetic bead method and integrates functions such as liquid transferring, blowing for uniform mixing and incubation, magnetic bead attraction and releasing, cleaning of sample addition needles, wind path filtering and ultraviolet sterilization, and automatic extension and retraction of a work station to a purification station to realize operations of target protein incubation, washing away of impurities, elution and the like of 12 samples. Contamination control is realized by a fully-sealed safety guard, a openable safety door, a wind path filtering system, an ultraviolet lamp and the like.

Figure 1:
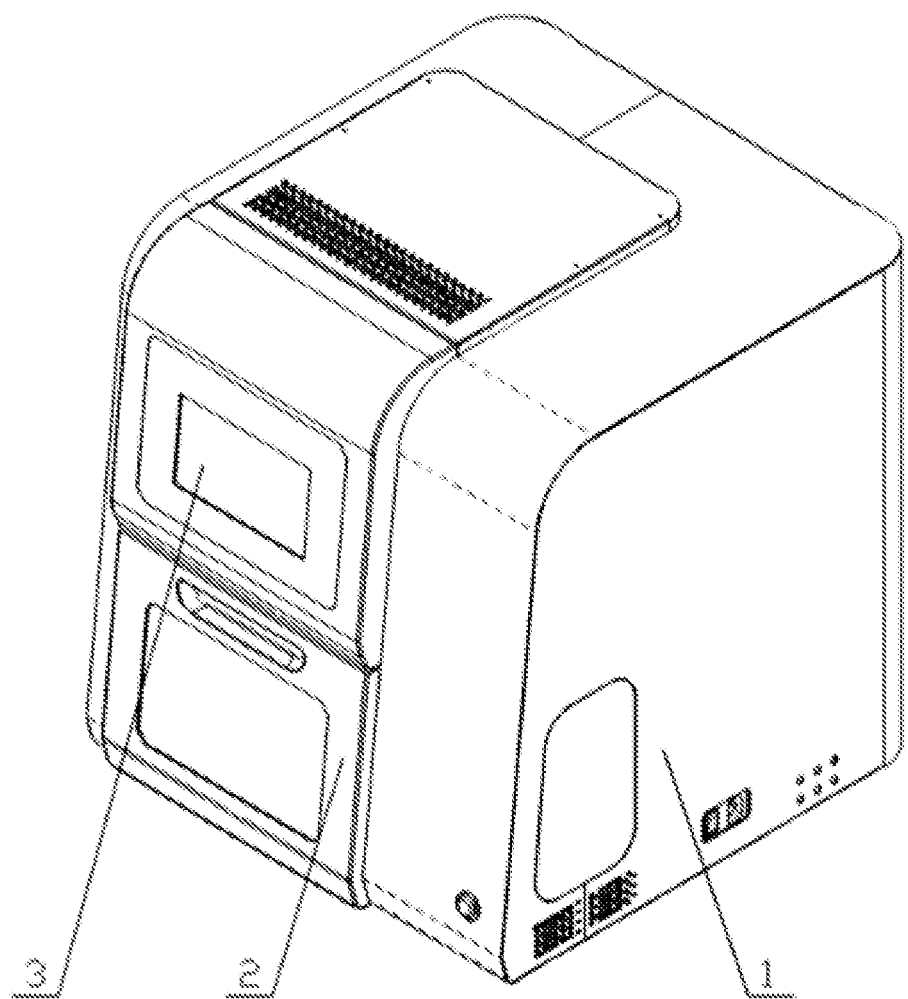
FIG. 1 illustrates a magnetic bead purification system according to an embodiment of the present invention.
Figure 2:
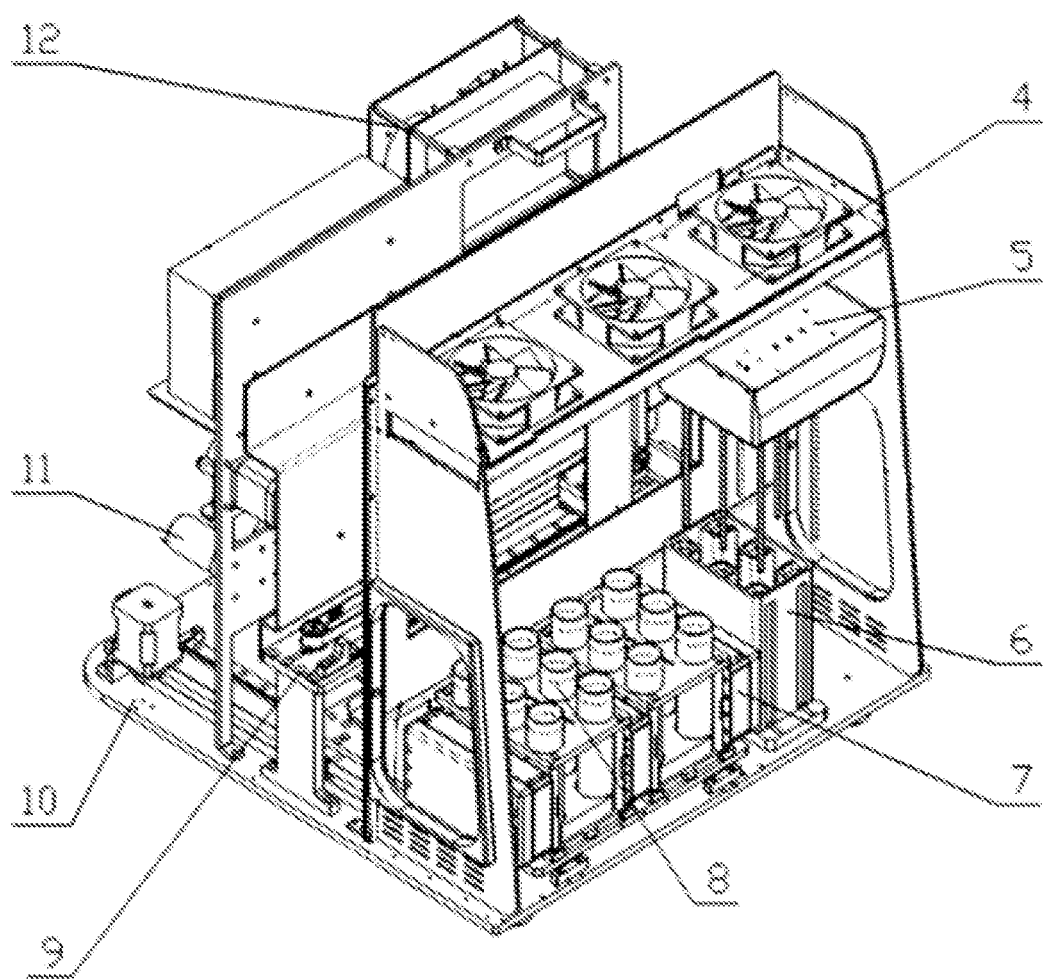
FIG. 2 illustrates an internal structural diagram of a magnetic bead purification system according to an embodiment of the present invention.

As shown in FIG. 1 and FIG. 2, the magnetic bead purification system according to the present invention may include the following modules: a housing 1, an openable safety door 2, a control display screen 3, a wind path filtering system 4, a variable-spacing sample addition needle group 5, a cleaning module 6, a purification magnetic separation system 7, a purification station system 8, a mechanical arm 9, a work bottom plate 10, a liquid path treatment system 11 and a control module 12.

Figure 3:
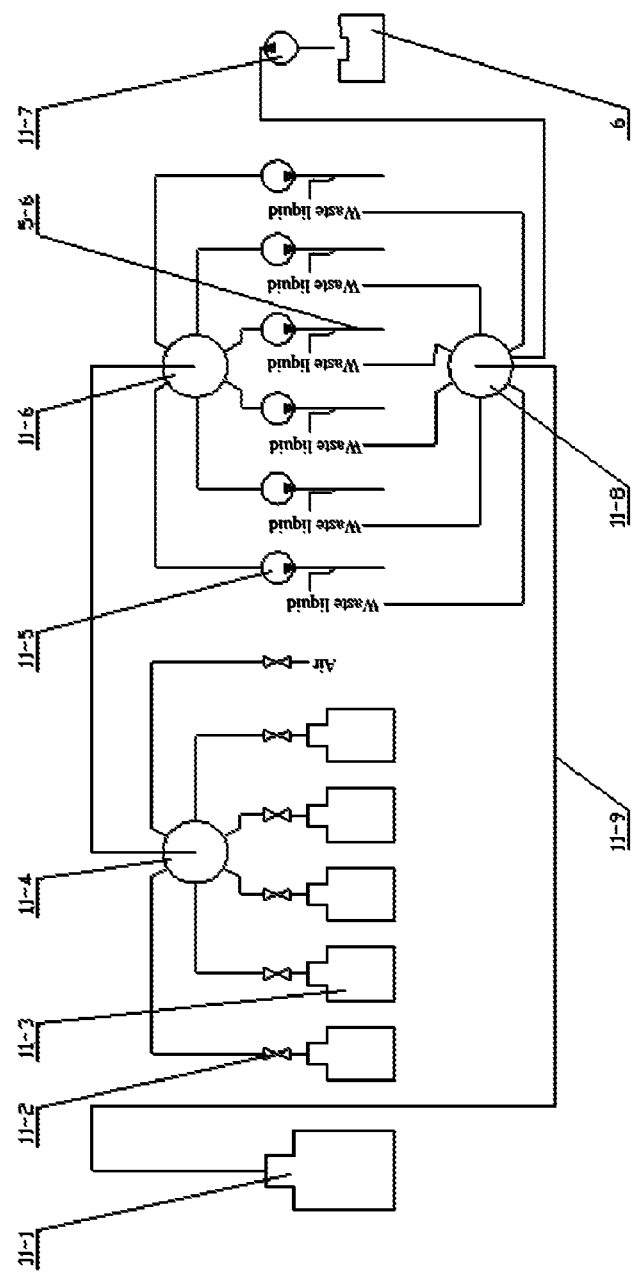
FIG. 3 illustrates a schematic diagram of a liquid path treatment system according to an embodiment of the present invention.

FIG. 3 illustrates a schematic diagram of the liquid path treatment system according to the present invention. The liquid path treatment system may include a waste liquid barrel 11-1, a two-way electromagnetic valve 11-2, a reagent barrel 11-3, a six-into-one liquid path valve 11-4, a liquid inlet peristaltic pump 11-5, a one-into-six liquid path valve 11-6, a sample addition needle 5-6, a waste liquid discharging peristaltic pump 11-7, a cleaning module 6, a seven-into-one liquid path valve 11-8 (seven liquid path passageways are merged into one liquid path passageway), a liquid path pipe 11-9, and a waste liquid discharging peristaltic pump connected to a sample addition needle liquid discharging passageway. The drawing is only an exemplary schematic diagram according to one embodiment of the present invention, and the liquid path treatment system can be adjusted according to specific applications. For example, the quantities and forms of the electromagnetic valve, the liquid path valve, the waste liquid barrel and the like can be appropriately changed as required. More specifically, the quantities of passageways of the foregoing liquid path valves can be appropriately changed according to specific applications.

The liquid path treatment system may be configured for reagent addition, spray rinsing of magnetic beads on a container wall, bubble blowing for uniformly mixing liquids, cleaning of sample addition needles, emptying of waste liquid in a container and in the cleaning module, and the like.

The liquid path treatment system at least includes one waste liquid discharging peristaltic pump connected to a waste discharging needle hole 5-6b, and the quantity of the waste liquid discharging peristaltic pumps connected to the waste discharging needle holes 5-6b is at most the same as the quantity of the sample addition needles 5-6.

The liquid path treatment system at least includes one liquid inlet peristaltic pump 11-5, and the quantity of the liquid inlet peristaltic pumps 11-5 may be the same as the quantity of the sample addition needles 5-6. The liquid inlet peristaltic pump 11-5 is connected to a sample addition needle hole 5-6c.

The main parts of the liquid path treatment system may be provided inside the housing. Preferably, the waste liquid barrel and the like may also be provided outside the housing, and a reagent source for supplying various reagents may also be provided outside the housing and connected to the liquid path treatment system through a pipeline.

The two-way electromagnetic valve 11-2 is configured to cut off or connect to a selected reagent liquid path passageway.

The six-into-one liquid path valve 11-4 that merges six liquid path passageways into one liquid path passageway cooperates with the two-way electromagnetic valve 11-2 to mainly select a required reagent or air, and the air is used for the sample addition needles to blow bubbles.

The one-into-six liquid path valve 11-6 that divides one liquid path passageway into six liquid path passageways is mainly configured to distribute the selected reagent or air to several sample addition needles 5-6.

Figure 4A:
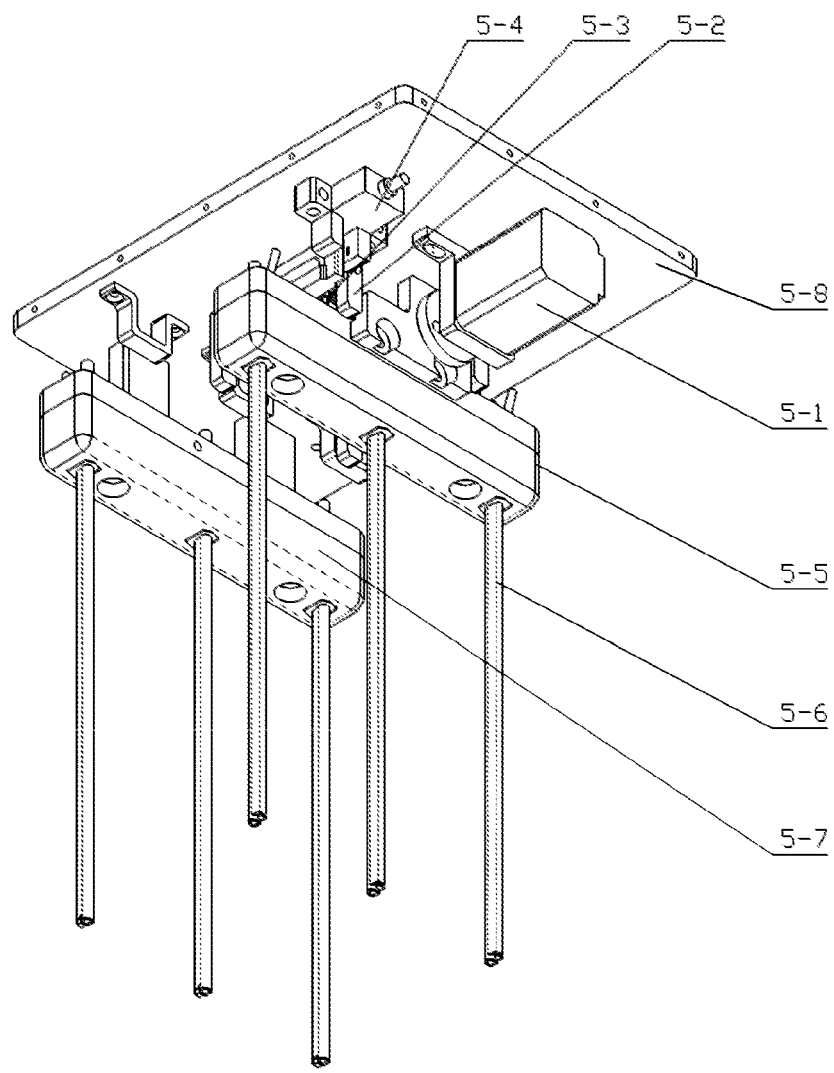
FIGS. 4A-4C illustrate a variable-spacing sample addition needle group according to an exemplary embodiment of the present invention.
Figure 4B:
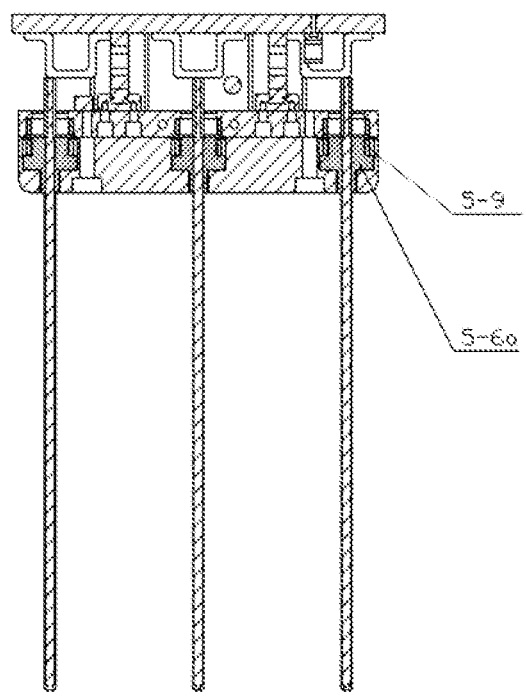
Figure 4C:
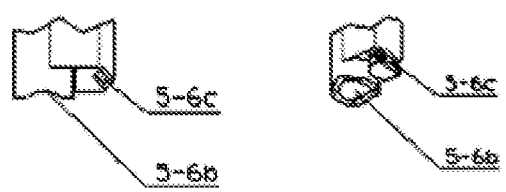

FIGS. 4A-4C illustrate the variable-spacing sample addition needle group according to an exemplary embodiment of the present invention. As shown in FIGS. 4A-4C, the variable-spacing sample addition needle group is fixed on a Z axis of the mechanical arm 9, thereby realizing up-and-down and left-to-right movements. In certain embodiments, the sample addition needle group may also be a fixed-spacing sample addition needle group.

The variable-spacing sample addition needle group includes at least one sample addition needle 5-6, one elastic mechanism 5-9, a fixed type sample addition needle fixing block 5-7 and a needle group bottom plate 5-8. Preferably, the variable-spacing sample addition needle group includes a plurality of sample addition needles 5-6.

When the variable-spacing sample addition needle group includes two variable-spacing sample addition needles 5-6, the variable-spacing sample addition needle group may further include a driving system 5-1, a mechanical limit 5-2, a control limit 5-4, a sliding mechanism 5-3 and a movable type sample addition needle fixing block 5-5. The sample addition needle group can realize flexible changes in the spacing between the movable type sample addition needle fixing block 5-5 and the fixed type sample addition needle fixing block 5-7 by controlling the driving system and a guide mechanism, so that the sample addition needles can adapt to different hole spacing.

When the variable-spacing sample addition needle group includes more variable-spacing sample addition needles 5-6, a plurality of movable type sample addition needle fixing blocks 5-5 and corresponding driving, guide and control systems may be set, thereby realizing flexible changes in the spacing between the movable type sample addition needle fixing blocks 5-5 and the fixed type sample addition needle fixing block 5-7 and between the plurality of movable type sample addition needle fixing blocks 5-5, so that the sample addition needles can adapt to different hole spacing.

The sample addition needle 5-6 may include a sample addition needle guide mechanism 5-6a, a waste discharging needle hole 5-6b and a sample addition needle hole 5-6c.

The elastic mechanism, for example, may include one spring and one guide mechanism.

The driving system, for example, may include a hydraulic cylinder, an air cylinder, or an electric motor.

The sliding mechanism, for example, may include a linear guide rail or a guide shaft guide sleeve.

In certain embodiments, the sample addition needles mounted on the same sample addition needle fixing block may also move relative to each other to adjust the spacing.

The elastic mechanism is configured for up-and-down trace movement of the sample addition needles, and can be in full contact with the bottom of the container to completely treat the liquid in the container without causing unduly high impact on the bottom of the container.

The waste discharging needle holes 5-6b are configured to discharge waste liquid; and the sample addition needle holes 5-6c are configured for reagent addition, spray rinsing of the container wall and bubble blowing. The reagents can rinse the magnetic beads on the container wall. The sample addition needles use a non-magnetic material, the surface of which is subjected to hydrophobic treatment. The waste discharging needle holes 5-6b and the sample addition needle holes 5-6c of the sample addition needles 5-6 are respectively communicated to the corresponding passageways of the liquid path treatment system.

Figure 5:
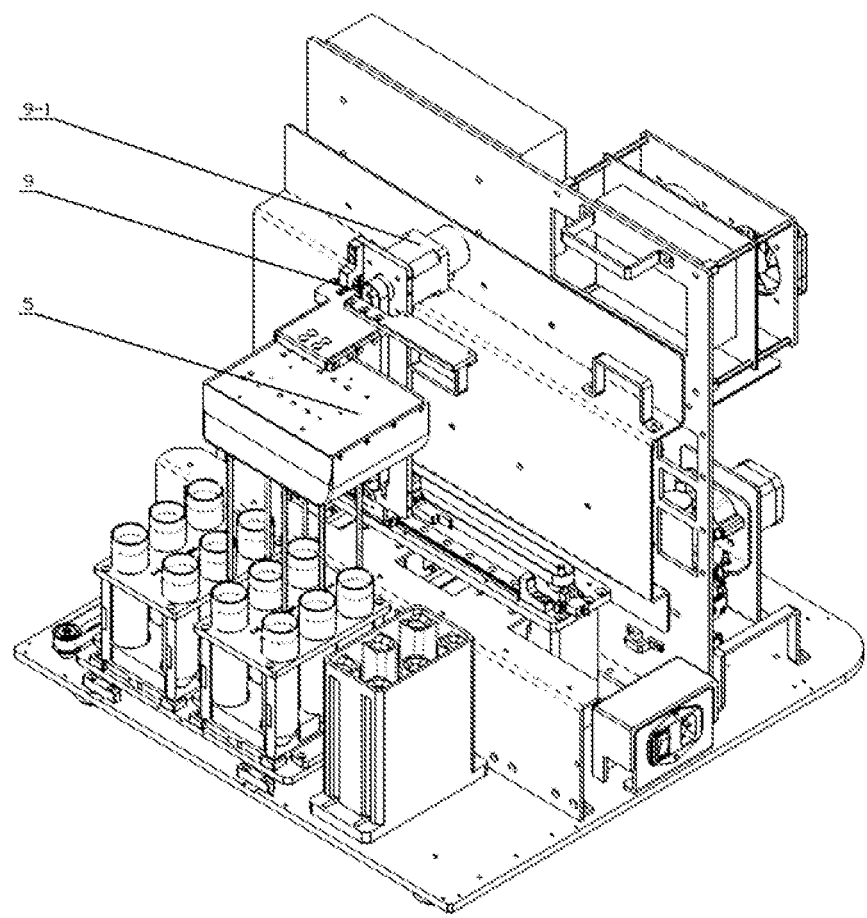
FIG. 5 illustrates a mechanical arm according to an exemplary embodiment of the present invention.

As shown in FIG. 5, the mechanical arm 9 at least includes an X axis for horizontal movement and a Z axis for perpendicular movement. The Z axis of the mechanical arm 9 is configured to fix the sample addition needle group. The mechanical arm 9 may include two driving systems, two sliding mechanisms and two limiting mechanisms which are respectively used for movements in a horizontal direction and a perpendicular direction. The driving system 9-1 of the Z axis for perpendicular movement is provided with a self-locking mechanism. The self-locking mechanism is configured to ensure that the sample addition needles cannot naturally fall off in any case.

The driving system, for example, may include a hydraulic cylinder, an air cylinder, or an electric motor.

The sliding mechanism, for example, may include a linear guide rail or a guide shaft guide sleeve.

The limiting mechanism, for example, may include a limiting switch and a mechanical limiting block.

Figure 6A:
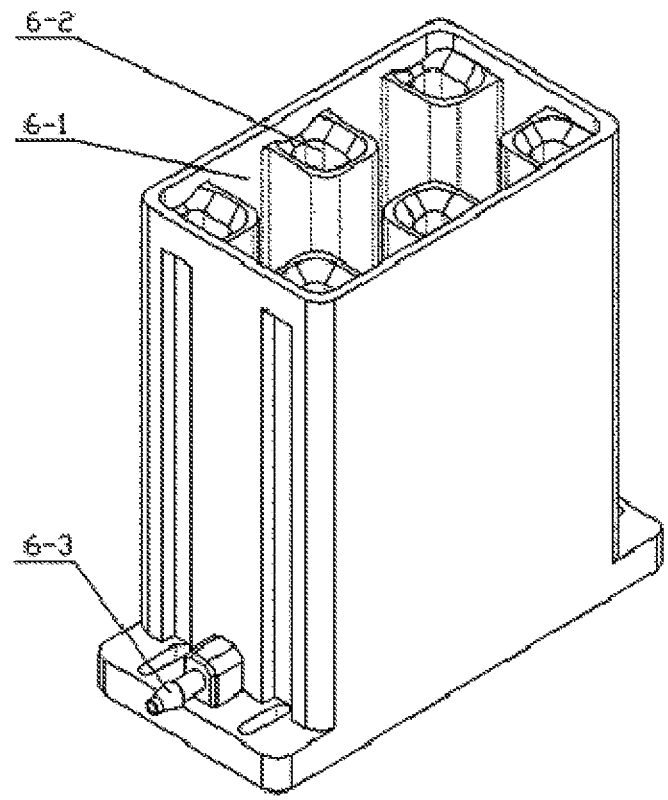
FIGS. 6A-6B illustrate a cleaning module according to an exemplary embodiment of the present invention.
Figure 6B:
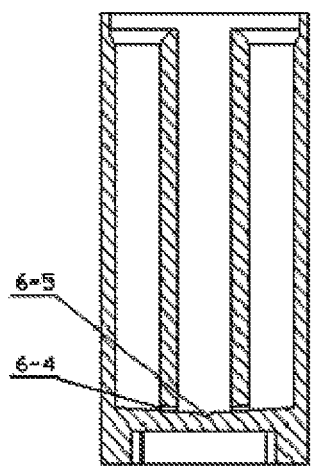

FIGS. 6A-6B illustrate a cleaning module for cleaning the sample addition needles 5-6 in the liquid path system, according to a preferable embodiment of the present invention. The cleaning module, for example, may be provided on the work bottom plate 10 of the magnetic bead purification system. The cleaning module, for example, at least includes a cleaning slot 6-1, one cleaning liquid addition hole 6-2 (paired with the sample addition needle), one liquid discharging hole 6-4 and one cleaning liquid discharging slot 6-5, and may further include one external liquid discharging interface 6-3. Preferably, the quantity and arrangement of the cleaning liquid addition holes 6-2 correspond to that of the sample addition needles 5-6.

During cleaning, the sample addition needles are inserted into the cleaning liquid addition holes 6-2. Since the rate of the liquid in the cleaning liquid addition holes flowing out of the liquid discharging holes 6-4 is less than the liquid addition rate when the sample addition needles add a cleaning liquid into the cleaning liquid addition holes 6-2, the cleaning liquid overflows from the tops of the cleaning liquid addition holes, and the overflowing liquid flows from the cleaning liquid discharging slot 6-5 to the external liquid discharging interface 6-3. The external liquid discharging interface 6-3 is connected to the waste liquid discharging peristaltic pump 11-7 to discharge the liquid in the cleaning module to the waste liquid barrel, thereby achieving the objective of cleaning the sample addition needles.

Figure 7A:
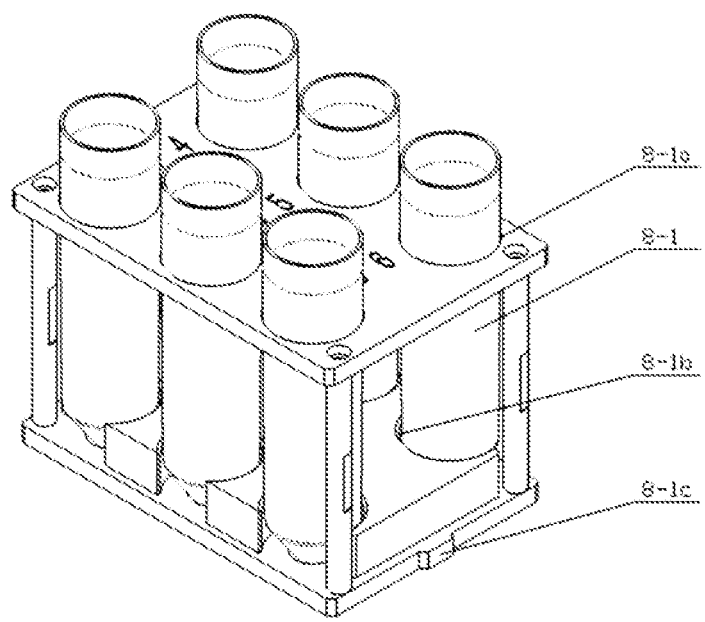
FIGS. 7A-7D illustrate a purification magnetic separation system and a purification station system according to an exemplary embodiment of the present invention.
Figure 7B:
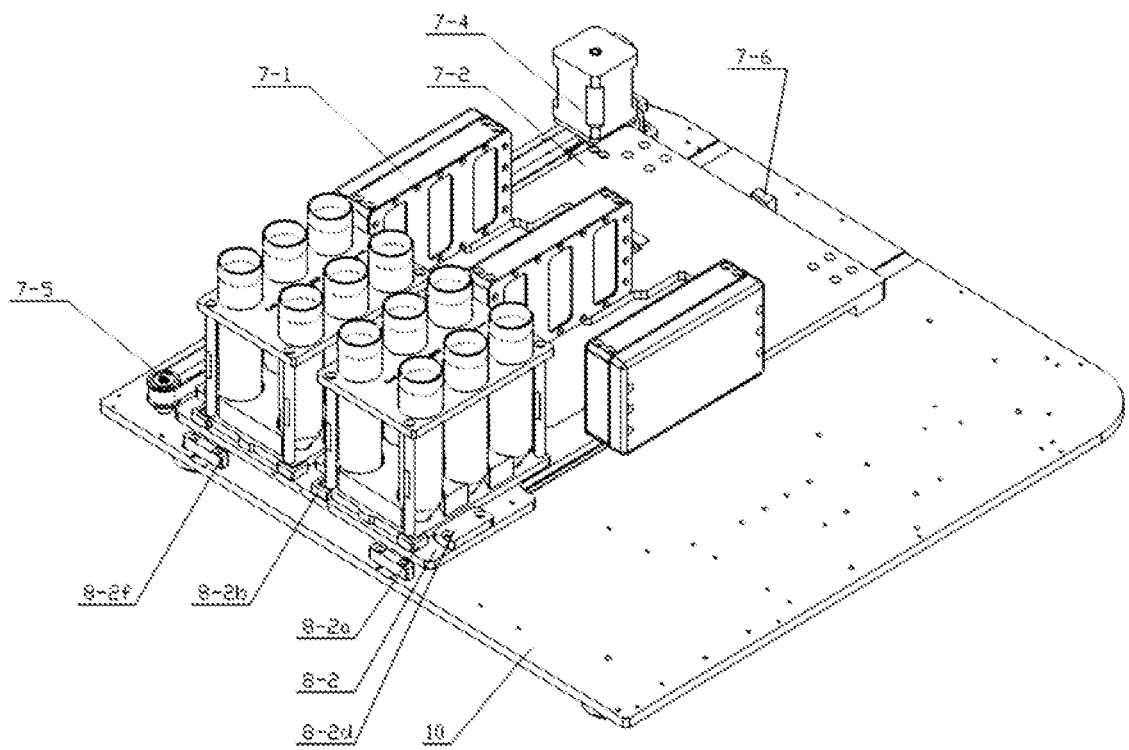
Figure 7C:
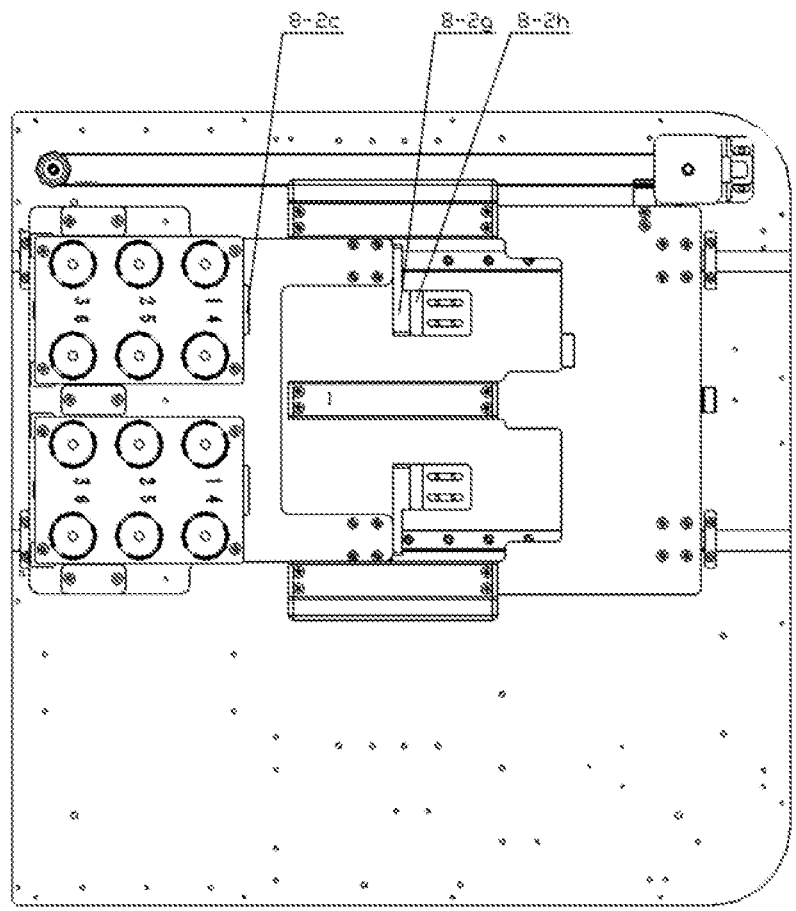
Figure 7D:
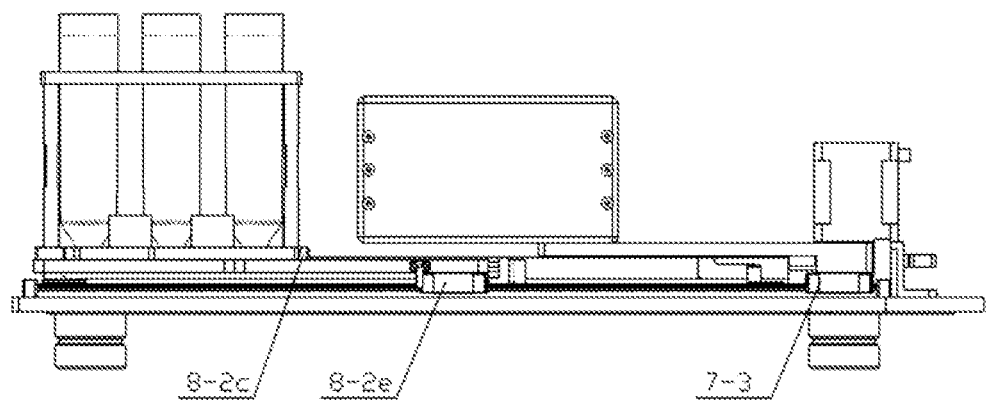

FIG. 7B illustrates the purification magnetic separation system 7 in the magnetic bead purification system according to a preferable embodiment of the present invention. As shown in FIG. 7B, the purification magnetic separation system 7 may include magnetic elements 7-1 for generating a magnetic field, a fixed plate 7-2, a sliding mechanism 7-3, a driving system 7-4, a transmission system 7-5 and a limiting mechanism 7-6. The size and the quantity of the magnetic elements 7-1 may be selected according to application requirements, and the magnetic element may be, for example, a permanent magnet (a magnet) and an electromagnet.

According to the embodiments shown in FIGS. 7A-7D, three magnetic elements 7-1 are provided respectively at two sides and a middle position relative to a moving direction of the purification station system. When a container containing a mixed liquid of the incubated crude proteins and the magnetic beads is loaded to the purification station system 8, and the purification station system 8 moves to a purification treatment position inside the housing, the magnetic elements 7-1 may be moved to the purification treatment position to apply a magnetic force. The magnetic force applied by the magnetic elements 7-1 to the purification treatment position acts on the magnetic beads in the container to attract the magnetic beads (for example, to attract the magnetic beads onto the container wall), so as to carry out corresponding subsequent operations.

In other embodiments, the arrangement of the magnetic elements 7-1 may be different. For example, they may be provided in such a manner that their width direction is perpendicular to the moving direction of the purification station system 8. When the purification station system 8 moves to the purification treatment position, the magnetic elements 7-1 may be moved to lean against the rear side of the purification station system 8. This arrangement is permissible as long as the magnetic force is enough.

When the attraction of the magnetic beads needs to be stopped, the magnetic elements 7-1 may be moved away from the purification treatment position, so as to leave far away from the magnetic beads to stop the application of the magnetic force. As long as the magnetic elements 7-1 are far enough and stop attracting the magnetic beads, it can be considered that the application of the magnetic force is stopped, even if there may still be a slight magnetic force acting on the magnetic beads or acting on the purification treatment position.

The purification treatment position refers to a region where the purification station system loading container carries out purification treatment in the housing, and is opposite to a loading position of the loading container outside the housing. The purification station system may move between the purification treatment position inside the housing and the loading position outside the housing.

In other embodiments, the magnetic elements 7-1 may be electromagnets which may be fixed around the purification treatment position, and the application of the magnetic force and the stop of the application of the magnetic force are controlled by controlling on and off of the magnetic elements.

The driving system, for example, may include a hydraulic cylinder, an air cylinder, or an electric motor.

The sliding mechanism, for example, may include a linear guide rail or a guide shaft guide sleeve.

The limiting mechanism, for example, may include a limiting switch and a mechanical limiting block.

As shown in FIGS. 7A-7D, the purification station system 8 includes a purification station bracket fixing module 8-2 and a purification station bracket 8-1. The purification station bracket 8-1 at least includes one purification station support, one upper side adaptation fixing hole 8-1a of container, one lower side adaptation fixing hole 8-1b of container, and a purification station bracket direction fixing block 8-1c. Preferably, the purification station bracket 8-1 includes a plurality of purification station supports, and a corresponding quantity of upper side adaptation fixing holes 8-1a of container and a corresponding quantity of lower side adaptation fixing holes 8-1b of container. Each purification station may hold one container filled with the mixed liquid of the incubated crude proteins and the magnetic beads.

The purification station bracket fixing module 8-2 at least includes one purification station bracket fixing block 8-2a, one purification station bracket fixing block 8-2b, one purification station bracket fixing block 8-2c, one magnetic attraction block 8-2d (the material of which is magnetically attractable, such as a magnet and carbon steel), one sliding mechanism 8-2e, one limiting block 8-2f, one movable type magnetic limiting block 8-2g and one fixed magnetic limiting block 8-2h.

The purification station bracket fixing block 8-2a, the purification station bracket fixing block 8-2b and the purification station bracket fixing block 8-2c may work cooperatively to effectively fix the purification station bracket. The purification station bracket direction fixing block 8-1c can guide the correct placement of the purification station bracket. The quantities and the positions of the purification station bracket fixing block 8-2a, the purification station bracket fixing block 8-2b and the purification station bracket fixing block 8-2c may be determined according to the quantity of purification station brackets 8-1 that need to be fixed.

In the embodiment shown in the figure, two purification station brackets 8-1 are fixed. Each purification station bracket 8-1 includes at least one adaptation hole for the purification container, preferably six adaptation holes for the purification container.

In the embodiment shown in the figure, the purification station system 8 may extend to a manual protein extraction station on the outer side of the instrument by a motion thrust of the purification magnetic separation system 7 and the sliding mechanism 8-2e. The purification station system 8 is pulled back to the purification station from the outer side of the instrument by an attraction force of the magnetic elements 7-1 in the magnetic attraction 8-2d and the magnetic separation system 7. In the process of pulling-back motion, the purification station system returns to the purification position by cooperation of the attraction forces of the movable type magnetic limiting block 8-2g and the fixed magnetic limiting block 8-2h. Of course, the purification station system 8 may also be independently provided with a driving device and a guide rail, and is pushed out and pulled back through the control system.

According to other embodiments, the purification station system 8 does not need to be provided with the purification station bracket 8-1, and may directly load a six-hole container on the purification station bracket fixing module 8-2 through a fixing device.

The openable safety door is provided with a limiting switch for controlling open and closed states of the door. If the openable safety door is opened by accident in an experimental process, the experiment process is ended. During ultraviolet sterilization, if the openable door is opened by accident, an ultraviolet lamp turns off.

The experiment process or operation method of the magnetic bead purification system according to the present invention is briefly described below according to the embodiments illustrated.

A purification process of the semi-automatic magnetic bead purification system according to the present invention mainly includes experiment preparation, endotoxin control and purification. Reagents used in the following operations mainly include: a reagent A: an impurity washing liquid, used for removing impurities (components except for the target proteins) from a liquid; a reagent B: a cleaning liquid, used for further removing the impurities from the liquid and change the acid and alkali environment of the liquid; a reagent C: an eluant, used for separating the magnetic beads and the target proteins; and a reagent D: aqueous alkali, used for components such as germs in a liquid pipeline in a liquid system and in the sample addition needles.

First, the experiment preparation may mainly include the following steps:

1. The system carries out self-inspection and resetting.

2. All pipelines (including pipelines between the reagent barrel and the two-way electromagnetic valve) in a liquid path are emptied.

Second, the endotoxin control may include the following steps:
1. The pipelines are filled with the reagent D for soaking, and the ultraviolet lamp is turned on at the same time.
2. The sample addition needles are cleaned with the reagent D, and then emptied.
3. The pipelines and the sample addition needles are cleaned with the reagent B, and then emptied.
4. Twelve centrifugal pipes filled with the mixed liquid of the incubated crude proteins and the magnetic beads, or one or two six-hole containers are manually put into the purification stations.

Third, the purification flow may include the following steps:
1. The magnets are moved close to the centrifugal pipes or the six-hole container to attract the magnetic beads.
2. When the magnetic beads are attracted to the magnets, six needles are used to intermittently blow air into the liquid in the front six centrifugal pipes or six-hole container for bubbling.
3. The magnets continue to attract the magnetic beads to promote full adsorption of the magnetic beads.
4. Six needles are put into the front six centrifugal pipes or six-hole container to suck supernate into the waste liquid barrel.
5. The pipelines and the needle heads are washed with the reagent A.
6. The steps 2 to 4 are repeated once to suck supernate in the rear six centrifugal pipes or six-hole container, and during the liquid suction, the needles may drop down discontinuously.
7. The pipelines and the needle heads are washed with the reagent A.
8. The magnets are moved away.
9. Six needles are used to add the reagent A into the 12 centrifugal pipes or six-hole container for the first time, and the addition is completed in two times, where the sample addition needles add the liquid in a suspended manner to ensure that the magnetic beads can be completely flushed away.
10. Six needles are used to intermittently blow air into the liquid in the front six centrifugal pipes or six-hole container for bubbling, so as to fully mix the magnetic beads.
11. The pipelines and the needle heads are washed with the reagent A.
12. Six needles are used to intermittently blow air into the liquid in the rear six centrifugal pipes or six-hole container for bubbling, so as to fully mix the magnetic beads, and stand.
13. The magnets are moved close to the centrifugal pipes or six-hole container to attract the magnetic beads.
14. When the magnetic beads are attracted to the magnets, six needles are used to intermittently blow air into the liquid in the rear six centrifugal pipes or six-hole container for bubbling.
15. The magnets continue to attract the magnetic beads to promote full adsorption of the magnetic beads.
16. Six needles are put into the rear six centrifugal pipes or six-hole container to suck supernate into the waste liquid barrel.
17. The pipelines and the needle heads are washed with the reagent A.
18. The steps 14 to 16 are repeated once to suck supernate in the front six centrifugal pipes or six-hole container, and during the liquid suction, the needles may drop down discontinuously.
19. The steps 5 to 16 are repeated three times.
20. The pipelines and the needle heads are washed with the reagent B.
21. The magnets are moved away.
22. Six needles are used to completely add the reagent B into the 12 centrifugal pipes or six-hole containers in two times, where the sample addition needles add the liquid in a suspended manner to ensure that the magnetic beads can be completely flushed away.
23. Six needles are used to intermittently blow air into the liquid in the front six centrifugal pipes or six-hole container for bubbling, so as to fully mix the magnetic beads, and stand.
24. The pipelines and the needle heads are washed with the reagent B.
25. Six needles are used to intermittently blow air into the liquid in the rear six centrifugal pipes or six-hole container for bubbling, so as to fully mix the magnetic beads, and stand.
26. The magnets are moved close to the centrifugal pipes or six-hole container to attract the magnetic beads.
27. When the magnetic beads are attracted to the magnets, six needles are used to intermittently blow air into the liquid in the rear six centrifugal pipes or six-hole container for bubbling.
28. The magnets continue to attract the magnetic beads to promote full adsorption of the magnetic beads.
29. Six needles are put into the rear six centrifugal pipes or six-hole container to suck supernate into the waste liquid barrel.
30. The pipelines and the needle heads are washed with the reagent B.
31. The steps 27 to 29 are repeated once to suck supernate in the front six centrifugal pipes or six-hole container, and during the liquid suction, the needles may drop down discontinuously.
32. The magnets are moved away.
33. The pipelines and the needle heads are washed with the reagent C.
34. Six needles are used to add the reagent C into the front six centrifugal pipes or six-hole container for the first time, where the sample addition needles add the liquid in a suspended manner to ensure that the magnetic beads can be completely flushed away.
35. After the reagent C is added completely, six needles are immediately used to intermittently blow air into the liquid in the front six centrifugal pipes or six-hole container for bubbling.
36. The pipelines and the needle heads are washed with the reagent C.
37. Six needles are used to add the reagent C into the rear six centrifugal pipes or six-hole container for the first time, where the sample addition needles add the liquid in a suspended manner to ensure that the magnetic beads can be completely flushed away.
38. After the reagent C is added completely, six needles are immediately used to intermittently blow air into the liquid in the front six centrifugal pipes or six-hole container for bubbling, and stand.
39. The magnets are moved close to the centrifugal pipes or six-hole container to attract the magnetic beads.
40. The openable safety door is opened to wait for an operator to manually transfer the proteins.

41. After the manual transferring of the proteins is completed, the openable safety door is closed.
42. The magnets are moved away.
43. The pipelines and the needle heads are washed with the reagent C.
44. Six needles are used to add the reagent C into the front six centrifugal pipes or six-hole container for the second time, where the sample addition needles add the liquid in a suspended manner to ensure that the magnetic beads can be completely flushed away.
45. After the reagent C is added completely, six needles are immediately used to intermittently blow air into the liquid in the front six centrifugal pipes or six-hole container for bubbling, and stand.
46. The pipelines and the needle heads are washed with the reagent C.
47. Six needles are used to add the reagent C into the rear six centrifugal pipes or six-hole container for the second time, where the sample addition needles add the liquid in a suspended manner to ensure that the magnetic beads can be completely flushed away.
48. After the reagent C is added completely, six needles are immediately used to intermittently blow air into the liquid in the front six centrifugal pipes or six-hole container for bubbling, and stand.
49. The magnets are moved close to the centrifugal pipes or six-hole container to attract the magnetic beads.
50. The openable safety door is opened to wait for an operator to manually transfer the proteins.
51. After the manual transferring of the proteins is completed, the openable safety door is closed.
52. The magnets are moved away.
53. The pipelines and the needle heads are washed with the reagent C.

It is to be noted that, the foregoing embodiments may be combined freely as required. The foregoing descriptions are merely exemplary implementations of the present invention. It is to be noted that a person of ordinary skill in the art may make various changes and improvements without departing from the principle of the present invention, and the changes and improvements shall fall within the protection scope of the present invention.

What is claimed is:

1. A magnetic bead purification system, comprising:
a housing;
a purification station system movable between a purification treatment position inside the housing and a loading position outside the housing, the purification station system being adapted to load a container filled with a mixed liquid of incubated crude proteins and magnetic beads;
a liquid path treatment system provided inside the housing, the liquid path treatment system being connectable to a reagent barrel and a waste liquid barrel;
a sample addition needle group connected to the liquid path treatment system so as to receive a reagent from the liquid path treatment system or to discharge a waste liquid to the liquid path treatment system, the sample addition needle group being movable within the housing;
wherein each sample addition needle of the sample addition needle group comprises a waste discharging needle hole configured to discharge waste liquid from said container at the purification treatment position and a sample addition needle hole configured to add reagents to said container at the purification treatment position; wherein the sample addition needle holes are further configured for spray rinsing of a container wall of said container and bubble blowing in said container at the purification treatment position; and
a purification magnetic separation system comprising a magnetic element, wherein the magnetic element is a permanent magnet, and wherein the purification magnetic separation system is controllable to apply a lateral magnetic force to said container at the purification treatment position inside the housing or stop the application of the lateral magnetic force by moving the magnetic element toward and away from the purification treatment position, and the magnetic element applies the lateral magnetic force to attract the magnetic beads onto the container wall of said container; and
wherein the purification station system comprises a magnetic attraction block so as to move from the loading position to the purification treatment position by the lateral magnetic force of the magnetic element of the purification magnetic separation system.

2. The magnetic bead purification system according to claim 1, wherein the purification magnetic separation system comprises a driving system, a sliding system and a transmission system, so as to move the magnetic element towards and away from the purification treatment position.

3. The magnetic bead purification system according to claim 1, wherein the purification station system comprises a sliding system, and is driven by a driving device to move from the purification treatment position to the loading position.

4. The magnetic bead purification system according to claim 1, wherein the purification station system comprises two purification station brackets, and each purification station bracket comprises at least one adaptation hole for a purification container.

5. The magnetic bead purification system according to claim 1, wherein the sample addition needle group is a variable-spacing sample addition needle group comprising a plurality of sample addition needles.

6. The magnetic bead purification system according to claim 5, wherein the variable-spacing sample addition needle group comprises a fixed type sample addition needle fixing block and a movable type sample addition needle fixing block which are each configured to mount a plurality of sample addition needles, and the movable type sample addition needle fixing block is movable to adjust a spacing between the sample addition needles in the sample addition needle group.

7. The magnetic bead purification system according to claim 6, wherein the variable-spacing sample addition needle group comprises more than one movable type sample addition needle fixing block.

8. The magnetic bead purification system according to claim 1, wherein the sample addition needle group comprises an elastic mechanism configured for up-and-down trace movement of the sample addition needles.

9. The magnetic bead purification system according to claim 1, wherein the magnetic bead purification system further comprises a mechanical arm provided inside the housing, and the sample addition needle group is mounted on the mechanical arm to realize movement.

10. The magnetic bead purification system according to claim 1, wherein the magnetic bead purification system comprises a cleaning module for cleaning the sample addition needles.

11. The magnetic bead purification system according to claim 10, wherein the cleaning module comprises cleaning liquid addition holes paired with the sample addition needles, a liquid discharging hole, a cleaning slot and a cleaning liquid discharging slot.

12. The magnetic bead purification system according to claim 1, wherein the magnetic bead purification system further comprises a control system; and the control system automatically controls operation of each component of the magnetic bead purification system according to settings.

13. The magnetic bead purification system according to claim 1, wherein the magnetic bead purification system further comprises a contamination control system, and the contamination control system comprises a wind path filtering system and an ultraviolet sterilization system.

14. The magnetic bead purification system according to claim 1, wherein the purification station system comprises a fixing device to load a six-hole container.

\* \* \* \* \*